(12) United States Patent
Montalbano et al.

(10) Patent No.: US 8,877,997 B2
(45) Date of Patent: Nov. 4, 2014

(54) QUENCH TOWER CATALYST RECOVERY

(75) Inventors: Joseph A. Montalbano, Bartlett, IL (US); John J. Senetar, Naperville, IL (US); Daniel A. Kauff, Arlington Heights, IL (US); Gurjit S. Sandhu, Hanover Park, IL (US)

(73) Assignee: UOP LLC, Des Plaines, IL (US)

( * ) Notice: Subject to any disclaimer, the term of this patent is extended or adjusted under 35 U.S.C. 154(b) by 58 days.

(21) Appl. No.: 13/324,034

(22) Filed: Dec. 13, 2011

(65) Prior Publication Data

US 2012/0157740 A1 Jun. 21, 2012

Related U.S. Application Data

(60) Provisional application No. 61/424,897, filed on Dec. 20, 2010.

(51) Int. Cl.
| | |
|---|---|
| *B01D 11/02* | (2006.01) |
| *C07C 1/20* | (2006.01) |
| *C07C 7/00* | (2006.01) |
| *B01D 47/06* | (2006.01) |

(52) U.S. Cl.
CPC . *C07C 1/20* (2013.01); *B01D 47/06* (2013.01); *C07C 7/00* (2013.01)
USPC .............................. 585/639; 422/261; 422/255

(58) Field of Classification Search
CPC .................................. B01D 11/02; C07C 7/00
USPC ......... 585/639, 640, 638, 609, 910, 804, 809, 585/903
See application file for complete search history.

(56) References Cited

U.S. PATENT DOCUMENTS

| | | | | |
|---|---|---|---|---|
| 2,889,265 | A * | 6/1959 | Borey et al. | 208/100 |
| 3,080,153 | A * | 3/1963 | Craig et al. | 261/22 |
| 2004/0152939 | A1* | 8/2004 | Pettigrew et al. | 585/809 |
| 2005/0027152 | A1 | 2/2005 | Van Egmond | |
| 2005/0238548 | A1 | 10/2005 | Van Egmond | |
| 2008/0146434 | A1* | 6/2008 | Corradi et al. | 502/21 |
| 2009/0325783 | A1 | 12/2009 | Myers | |

OTHER PUBLICATIONS

Elewady et al. "Anion Surfactants as Corrosion Inhibitors for Aluminum Dissolution in HCI Solutions." International Journal of Electrochemcial Science. 3 (2008) 177-190.*

* cited by examiner

*Primary Examiner* — In Suk Bullock
*Assistant Examiner* — Sharon Pregler
(74) *Attorney, Agent, or Firm* — Arthur E Gooding

(57) ABSTRACT

A process and apparatus is presented for the removal of solid particles from a gas stream. The process and apparatus includes adding a second stream of liquid that is sprayed over the openings in trays in a quench tower. The second spray stream provides for a veil of liquid to wash out solid particles from the vapor stream.

10 Claims, 1 Drawing Sheet

QUENCH TOWER CATALYST RECOVERY

CROSS-REFERENCE TO RELATED APPLICATION

This application claims benefit of U.S. Provisional Application No. 61/424,897 filed on Dec. 20, 2010.

FIELD OF THE INVENTION

The present invention relates to the conversion of methanol to olefins. In particular, the invention relates to the recovery of catalyst used in the methanol to olefins conversion process.

BACKGROUND OF THE INVENTION

The traditional method of olefin production is the cracking of petroleum feedstocks to olefins. The cracking of petroleum feedstocks is done through catalytic cracking, steam cracking, or some combination of the two processes. The olefins produced are generally light olefins, such as ethylene and propylene. There is a large market for the light olefin products of ethylene and propylene. As petroleum feedstocks from crude oil face increasing prices it is advantageous to provide for other sources of ethylene and propylene. It is also known that olefins can be produced from oxygenates. The most common conversion of oxygenates to olefins is the production of light olefins from methanol, wherein methanol can be produced from other sources, including biomass, and natural gas.

The process of converting oxygenates to olefins is an important process for utilizing oxygenates, such as methanol, and converting them to higher value products such as monomers for plastics, such as ethylene and propylene. The process of converting oxygenates to olefins is a catalytic process, and the catalyst is usually a molecular sieve catalyst. Among the molecular sieves that are useful for the catalytic process are ZSM-type molecular sieves, but more particularly, it has been found that silico-aluminophosphate (SAPO) molecular sieves work well in the process.

SAPOs are synthesized by forming a mixture containing sources of silicon, aluminum, and phosphorus mixed with an organic template, and then crystallizing the molecular sieve at reaction conditions. Many factors affect the form the molecular sieve takes, including the relative amounts of the different components, the order of mixing, the reaction conditions, e.g. temperature and pressure and the choice of organic template.

However, MTO catalysts are expensive and susceptible to erosion. The erosion creates catalyst fines that are carried out in the MTO reactor effluent stream. The catalyst fines create a problem for downstream equipment.

SUMMARY OF THE INVENTION

The present invention improves the removal of solid catalyst fines from a reactor effluent stream. The fines when carried through to downstream equipment present maintenance and operational problems that can incur significant expenses. The present invention is a process for quenching an effluent stream from a hydrocarbon reactor that uses a catalyst. The effluent stream is passed to a quench tower. A circulating water stream is passed to the quench tower and cascades down through the tower contacting the effluent stream. A second water stream is passed to the quench tower and generates a spray of water droplets for contacting the effluent stream. The spray is directed to vapor channels where the effluent stream flows. The effluent stream is contacted with the first water stream cascading through the tower, and is contacted with the second stream of spray droplets, thereby creating a quenched effluent stream having a reduced solid particle content, and a water and solid outlet stream.

In one embodiment, the reactor effluent stream is the effluent stream from a methanol to olefins reactor. The quench tower includes disc and donut trays where the first stream of water creates a veil of water for the effluent stream to pass through as the effluent stream flows through the quench tower. One aspect for improving the contact and wetability of the solid catalyst particles is to include a surfactant in the circulating water streams.

Other objects, advantages and applications of the present invention will become apparent to those skilled in the art from the following detailed description and drawings.

DETAILED DESCRIPTION OF THE INVENTION

Figure 1:
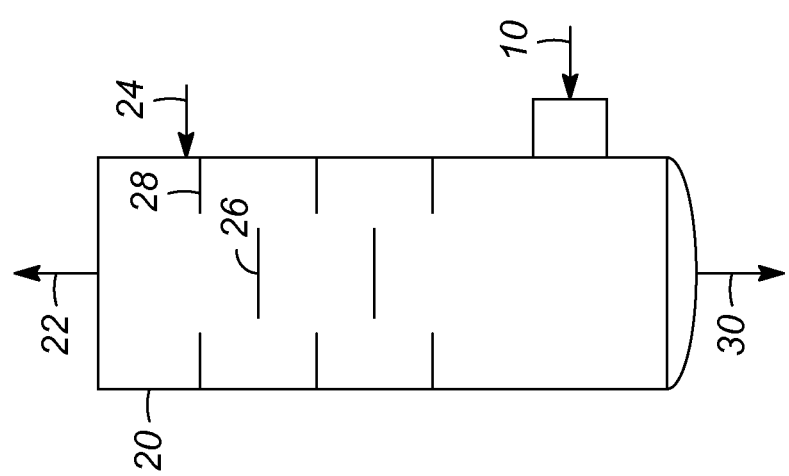
FIG. 1 is the current design for a quench tower.

Many hydrocarbon processes involve the cooling and/or quenching of a product effluent stream. This can include the quenching of an intermediate process stream before the stream is passed to a subsequent process unit. One area where quenching is a factor in processing an effluent stream is the methanol to olefins (MTO) conversion process. The MTO process involves contacting a methanol feed stream with a catalyst in a reactor, thereby generating an effluent stream. The MTO reactor effluent contains catalyst fines and the current process includes a quench tower, as shown in FIG. 1. The process includes passing an effluent stream 10, comprising the reactor vapor to the quench tower 20, where the vapor flows up the tower 20 and through a vapor exit port 22. An aqueous quench stream 24 flows into the tower 20 and down over a series of disc 26 and donut 28 trays. The quench stream is intended to be captured catalyst fines in the bottom of the tower 20. The quench stream with fines 30 is collected, filtered and pumped around back to the quench stream inlet 24. However, it has been found that fine catalyst particles are currently passing through the top of the tower. Filters and pipes have shown a hard concrete-like material that is expected to be catalyst fines. These fines foul downstream equipment up to the product compressor. In addition, it has been found that catalyst fines still have some activity and can be recycled to the reactor from which they originate. This can increase the cycle time of a reactor.

Figure 2:
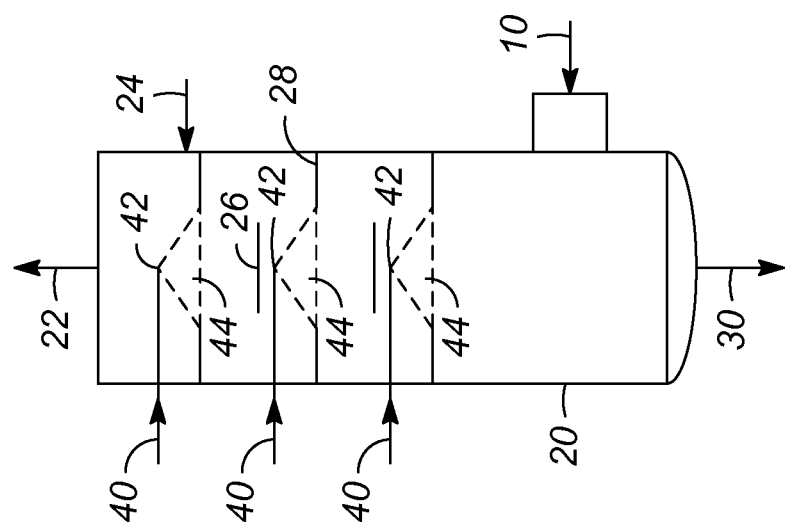
FIG. 2 is an improved design for the quench tower with counter-current flow.

The present invention is an improved quench tower process and design to further remove catalyst fines from the reactor effluent vapor stream. The process, as shown in FIG. 2, includes the addition of spray streams to create a liquid shield that further knocks out catalyst fines. The process includes passing a reactor effluent stream 10 into a quench tower 20. A circulating water stream 24 is passed to the quench tower 20, where the water cascades down a series of disc 26 and donut 28 trays with the vapor passing through the cascading water. The process further includes passing a second water stream 40 to a series of spray nozzles 42 to generate a spray 44 of water droplets. The nozzles 42 are positioned such that the spray 44 is spread over the openings in the donut 28 trays. The effluent stream as it rises though the quench tower 20 contacts the cascading water stream and the spray 44 from the nozzles.

The quenched effluent stream 22 leave the top of the quench tower 20, and the water and solids stream 30 leaves the bottom of the tower 20.

While the process described above is with a tower having disc and donut trays, the process can include other tray designs, where the first stream cascades down the tower over trays, and possible traveling back and forth across the tower. The second stream is sprayed over sections of the trays where the vapor flows upward in a counter-current flow relative to the flow of the quench water.

The process can further include passing the quenched effluent stream 22 through a cyclonic device (not shown). A cyclonic device will provide a mechanical means to remove residual solid catalyst fines that manage to pass through the two quench streams. This generates a quenched stream with reduced solid catalyst fines.

Figure 3:
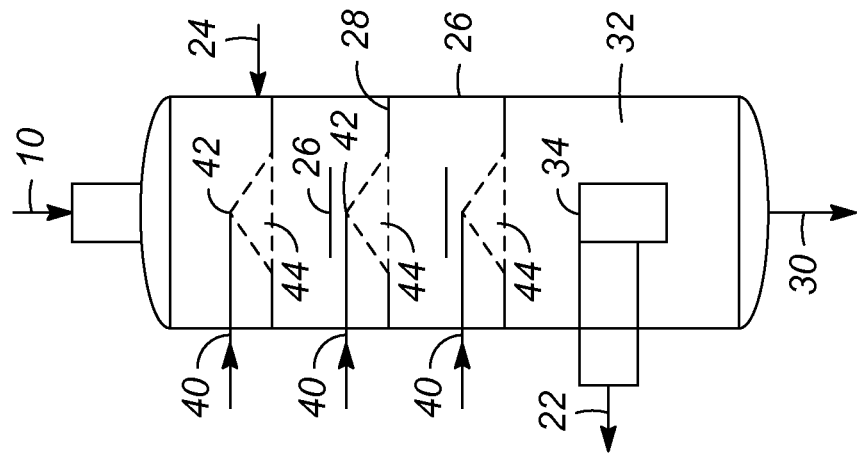
FIG. 3 is an improved design for the quench tower with co-current flow.

In a second embodiment, the invention provides for a co-current flow quench tower, as shown in FIG. 3. The process includes a reactor vapor inlet stream 10 entering at the top of the quench tower 20. A circulating water stream 24 is passed into the tower 20 and cascades down a plurality of trays 26, 28, wherein a veil of water is created and the reactor vapor is contacted with the veil of water as the vapor flows past the trays 26, 28. The flow of the water 24 and the reactor effluent stream 10 flow down through the tower 20 into a lower section of the tower 32, where the vapor and liquid disengage, forming an quenched vapor stream 22 and a liquid wash stream 30. The quenched vapor stream 22 exits a port on the side of the tower 20 below the last tray, and the wash stream 30 exits the bottom of the tower 20. The lower section 32 of the tower can include a hood 34 for collecting the vapor as it disengages from the liquid. The hood 34 will collect vapor as it flows in an upward direction while separating from the liquid that continues to flow in a downward direction.

In the second embodiment, the process further includes a plurality of spray nozzles 42. The nozzles 42 are on the end of inlets for a second water stream 40 where each nozzle generates a spray stream 44, creating a veil of liquid droplets to further improve contact with the reactor vapor 10 and to remove solid particle catalyst fines. The preferred tray design choice is a disc 26 and donut 28 trays, where the disc 26 trays extend over the openings of the donut 28 trays. The spray nozzles 42 are disposed over the openings to the donut trays 28, and are positioned beneath the disc trays 26. The nozzle design and position are selected to provide for a veil of spray droplets 44 that extend across the openings of the donut trays 28.

The process is improved if the particles can be readily wetted with the circulating water stream 24. In one embodiment, a surfactant is added to the water stream 24, and to the second stream 40 to improve the wetability of the catalyst fines. The ability to pick up water by the fines increases the removal of the small solid particles that remain in the reactor effluent stream 10. The choice of surfactant can be affected by a number of process factors, including, but not limited to, the volatility of the surfactant, the molecular weight of the surfactant, etc.

The co-current flow embodiment can include a second tower (not shown). In the co-current flow having a second tower, the first tower is used primarily to knock out the solid catalyst fines, and the second tower is used to quench the reactor effluent stream as the effluent stream leaves the first tower. In the embodiment with two towers, the first tower is to primarily capture catalyst fines, with the second tower performing the quenching function.

In another embodiment, the process can pass a recirculating water stream 24 into the quench tower 20. The reactor effluent stream 10 is passed into the quench tower 20. The quench tower 20 utilizes a packing material and a distributor tray having large openings instead of trays. The packing material has large openings, such as large slotted rings or large Rashig rings. The process further includes passing a second liquid stream 40 into the tower 20 where the second liquid stream creates a veil of spray droplets 44 over the large openings in the distributor tray. In the embodiment utilizing packed beds, the quench tower 20 can include a plurality of packed beds, with a distributor tray disposed over each packed bed, and a spray nozzle, or set of spray nozzles disposed over each distributor tray, where the spray nozzles provide a veil of liquid drops over the openings of each distributor tray.

One embodiment of the invention is an apparatus for the quenching of a vapor stream containing solid particles. The apparatus includes a quench tower having a vapor inlet proximate to the bottom of the tower, a quench liquid inlet proximate to the top of the tower, a quenched vapor stream outlet proximate to the top of the tower and a liquid outlet proximate to the bottom of the tower. The tower includes a plurality of trays for the quench liquid to cascade down the tower forming a liquid veil through which the vapor stream passes. In a preferred embodiment, the trays comprise disc and donut trays in an alternating arrangement. The apparatus further includes a plurality of spray devices for admitting a second liquid stream into the quench tower. The spray devices are disposed to create a veil of liquid droplets over the openings in the trays, and in particular over the openings in the donut trays.

The process can include additional features. Among the features included are the use of a pipe restriction with the water spray to further expose the solid catalyst particles to the water. This is a feature for smaller reactor systems. The reactor effluent stream can be directed to enter the quench tower in a manner that is tangential to the tower such that the reactor effluent flow into the reactor is in a circumferential flow. This produces centripetal forces to facilitate the separation of the solids from the reactor effluent stream.

Other possible design features include the addition of internal vanes in the lower section of the quench tower. The vanes can provide a swirl component to the effluent gas flow and facilitate the separation of particles from the cyclonic motion of the effluent gas flow.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for quenching an effluent stream from a methanol to olefins reactor, comprising:
    passing the effluent stream to a quench tower;
    passing a circulating water stream to the quench tower, and cascading the water stream down the tower, wherein the quench tower comprises a series of disc and donut trays for the water to cascade down the tower;
    spraying a second water stream to generate a spray of water droplets, where the spray is directed to vapor channels where the effluent stream flows, wherein the spray is directly spread over the openings in trays disposed in the quench tower for contacting the spray with the effluent stream; and
    contacting the effluent stream with the water stream and the spray of water droplets to remove catalyst particles from the effluent stream, thereby creating a quenched effluent stream and a water and solids outlet stream.

2. The process of claim 1 wherein the spray is directed to the donut openings of the donut trays.

3. The process of claim 1 wherein the water stream flows downward through the quench tower and the effluent stream flows upward through the quench tower.

4. The process of claim 1 wherein the water stream flows downward through the quench tower and the effluent stream flows downward through the quench tower.

5. The process of claim 4 wherein the quenched stream is passed to a second tower.

6. The process of claim 1 further comprising adding a surfactant to the circulating water stream and to the second water stream to increase the wetting capability of the quenching water.

7. The process of claim 1 further comprising passing the quenched effluent stream through a cyclonic device thereby creating a solid particle stream and a quenched effluent stream with reduced catalyst fines.

8. The process of claim 1 wherein the quench tower includes a plurality of trays where the water stream flows downward through the tower and the effluent stream flows upward through the tower, further comprising:
passing the circulating water stream to the quench tower, and cascading the water stream down the tower, wherein the quench tower includes a plurality of disc and donut trays for the water to flow down through the donut tray openings and over the disc trays, and where the circulating water stream is passed into the quench tower above the trays.

9. The process of claim 8 further comprising adding a surfactant to the circulating water stream and to the second water stream to increase the wetting capability of the quenching water.

10. The process of claim 8 further comprising passing the quenched effluent stream through a cyclonic device thereby creating a solid particle stream and a quenched effluent stream with reduced catalyst fines.

\* \* \* \* \*